US006413908B1

(12) United States Patent
Reekmans et al.

(10) Patent No.: US 6,413,908 B1
(45) Date of Patent: Jul. 2, 2002

(54) AGROCHEMICAL SURFACTANT COMPOSITIONS

(75) Inventors: Steven Irene Jozef Reekmans, Brussels; Mahroussa Auda, Sint Denijs Westrem; Frank Dirk Jozef Hartmann, Wetteren, all of (BE)

(73) Assignee: Imperial Chemical Industries plc, London (GB)

( * ) Notice: Subject to any disclaimer, the term of this patent is extended or adjusted under 35 U.S.C. 154(b) by 0 days.

(21) Appl. No.: 09/373,493

(22) Filed: Aug. 12, 1999

Related U.S. Application Data

(63) Continuation of application No. PCT/GB98/00459, filed on Feb. 13, 1998.

(30) Foreign Application Priority Data

Feb. 14, 1997 (GB) .............................. 9703054

(51) Int. Cl.$^7$ ................................. A01N 3/02
(52) U.S. Cl. ...................................... 504/116
(58) Field of Search ......................... 504/116

(56) References Cited

U.S. PATENT DOCUMENTS 5,710,104 A * 1/1998 Magin et al. ............... 504/206

FOREIGN PATENT DOCUMENTS

| EP | 485207 | * 5/1992 |
| WO | 97 00010 | 1/1997 |

OTHER PUBLICATIONS

Database Caplus Davis: "Solid adjuvants based on urea–surfactant adducts" XP002067870 AN 1996: 668072 DN 125: 320535 see abstract & ASTM Spec. Tech. Publ, 1996 pp. 161–167 STP1268.

* cited by examiner

Primary Examiner—Alton Pryor
(74) Attorney, Agent, or Firm—Pillsbury Winthrop LLP

(57) ABSTRACT

Aqueous agrochemical compositions of dispersed phase agrochemicals, particularly phytoactives, such as growth regulators and/or herbicides, or pesticides, such as insecticides, fungicides, or acaricides, include as adjuvant a branched primary alcohol alkoxylate of the formula (1): $[CH_3.(CH_2)_n][CH_3.(ch_2)_m].CH.[(CH_2)_p.O.(AO)_q.H]$ where n, m, p, AO and q have defined meanings are disclosed. In the compositions, the agrochemical can be present as dispersible granules or dissolved or dispersed in an oil. The compositions can be concentrates or diluted sprayable compositions. A particularly convenient form of composition is as dispersible granules.

19 Claims, No Drawings

AGROCHEMICAL SURFACTANT COMPOSITIONS

This is a continuation under 35 U.S.C. Section 120 of International application Serial Number PCT/GB98/00459 filed on Feb. 13, 1998 which application designates the U.S.

This invention relates to agrochemical compostions including adjuvants, and in particular to compositions which contains at least one adjuvant surfactant and a dispersed phase agrochemical.

Agrochemical adjuvants are compounds or mixtures of compounds, which often are or include surfactants, used in the agrochemical industry to enhance the activity or effectiveness of an agrochemical in a formulation. We use the phrase "adjuvant surfactant" to refer to surfactants which have (alone or in combination with other materials) adjuvant effects in agrochemical formulations.

The present invention is directed to compositions including adjuvant surfactants, and specifically to branched primary alcohol alkoxylates, which have interesting adjuvant activity. The adjuvant surfactants can be included in agrochemical formulations by inclusion in agrochemical concentrates or they can be included in spray formulations by tank mixing.

The present invention accordingly provides an aqueous agrochemical composition which includes a dispersed phase agrochemical and as an adjuvant a branched primary alcohol alkoxylate of the formula (I):

$$[CH_3.(CH_2)_n][CH_3.(CH_2)_m].CH.[(CH_2)_p.O.(AO)_q.H] \quad (1)$$

where n and m, are each independently from 1 to 13; and p is 1 or 2; such that n+m+p is from 8 to 18;

AO is an alkylene oxide residue having from 2 to 4 carbon atoms and is particularly an ethylene oxide residue, a propylene oxide residue or a mixture of ethylene oxide and propylene oxide residues; and q is from 2 to 30.

We use the phrase "dispersed phase agrochemical" to refer to a material which has agrochemical activity and which is substantially insoluble in water and is used in the form a dispersion of particles of or including the solid or liquid agrochemical in water. Solid dispersed particles can be of the agrochemical itself or of the agrochemical supported on mixed with other solid (insoluble) material(s). Similarly, liquid dispersed particles can be of the agrochemical itself or of the agrochemical dissolved or dispersed (as a solid or as a solution in a second non-aqueous internal liquid phase) in a non-aqueous liquid. The aqueous formulations containing dispersed agrochemical are typically applied to plants, or the immediate environment of plants e.g. the soil around the plants, by spraying.

We refer to various types of compositions and formulations. "Agrochemical compositions" are compositions including an active agrochemical and refers all forms of compositions including concentrates and spray formulations. "Spray formulations" are aqueous agrochemical formulations including all the components which it is desired to apply to the plants or their environment in a form and at a concentration (dilution) appropriate for spraying. Spray formulations can be made up by simple dilution of concentrates containing desired components (other than water), or by mixing of the individual components, or a combination of diluting a concentrate and adding further individual components or mixtures of components. Typically such end use mixing is carried out in the tank from which the formulation is sprayed or a holding tank for filling the spray tank and commonly such mixing and mixtures are called tank mixing and tank mixtures. "Agrochemical concentrates" are agrochemical compositions, which may be aqueous or non-aqueous, which are designed to be diluted with water (or a water based liquid) to form the corresponding spray formulations and include such compositions in liquid form such as solutions, emulsions or dispersions and in solid form, especially in water dispersible solid form, such as granules or powders. "Emulsifyable concentrates" are liquid "agrochemical concentrates" including the active agrochemical in solution or dispersion, usually also including dispersant and/or emulsifier surfactant, which readily emulsify on dilution in water, typically with no more than gentle stirring.

In compounds of the formula (I), n and m are desirably each independently at least 2 and not more than 12, p is desirably 1 and the total number of carbon atoms in the branched alkyl residue is desirably from 8 to 18, particularly 10 to 14 and especially is 12 (corresponding to n+m+p from 5 to 15, particularly 7 to 11 and especially 9). The alkylene oxide groups are desirably all ethylene oxide residues or mixtures of ethylene oxide and propylene oxide residues, desirably having a molar ratio of ethylene oxide residues to propylene oxide residues of from 1:5 to 10:1. When the alkylene oxide residues are mixed ethylene oxide and propylene oxide residues, the polyoxy-alkylene chain can be a random or block copolymeric chain. Within the range 2 to 30, q is desirably 5 to 20 and generally q is larger where the number of carbon atoms in the branched alkyl residue is larger. The number of units in the polyoxyalkylene chain, 'q', is an average value and may be non-integral.

The alkoxylate compounds of the formula (I) used in this invention can be made by alkoxylation of the corresponding branched primary alcohols under conventional alkoxylation conditions, typically under alkali catalysis, particularly alkoxide catalysis e.g. using NaOH or KOH to form alkoxide in situ). The branched primary alcohols can be substantially wholly branched alcohols as can be made by the guerbet process e.g. 2-butyloctanol, 2-butyidecanol, 2-butyidodectanol, 2-hexyl-octanol, 2-hexyldecanol, 2-hexyldodectanol and 2-octyldecanol; or they can be mixtures of the above branched primary alcohols with linear primary alcohols, containing similar numbers of carbon atoms, such as can be made by the oxo process starting with internal olefins. The proportion of branched primary alcohol of the formula (I) in the alcohol used as the starting material for alkoxylation is desirably at least 40% and more usually at least about 50%.

Where the agrochemical is present in the aqueous end use formulation as solid particles, most usually it will be present as particles mainly of active agrochemical. However, if desired, the active agrochemical can be supported on a solid carrier.

Where the dispersed phase is a non-aqueous liquid, it will typically be an oil. The oil may be or include a mineral oil, including aliphatic (paraffin) mineral oils and aromatic mineral or synthetic oils, such as those sold under the trade name Solvesso; an optionally hydrogenated vegetable oil, such as an optionally hydrogenated cotton seed oil, linseed oil, mustard oil, neem oil, niger seed oil, oiticica oil, olive oil, palm oil, palm kernel oil, peanut oil, perilla oil, poppy seed oil, rape seed oil, safflower oil, sesame oil, or soybean oil; an ester oil (a synthetic ester oil), especially a $C_{1-6}$ ester of a $C_{8-22}$ fatty acid, especially a $C_{12-18}$ fatty acid, or a mixture of esters, such as methyl laurate, heptadecanoate, heptadecenoate, heptadecadienoate, stearate or oleate, and in particular methyl laurate and oleate; N-methylpyrrolidone; or an isoparaffin; or a mixture of such oils.

The adjuvant surfactant of the formula (I) will typically be used in an amount in proportion to the amount of the active agrochemical. In spray formulations (typically at a spray application rate of from 10 to 500 l.ha$^{-1}$) typical agrochemical concentrations are in the range from about 0.001 to about 1% by weight of the spray formulation and in such systems the adjuvant surfactant will typically be used at a concentration of from 0.01 to 2%, more usually from 0.03 to 0.5%, by weight of the spray formulation, approximately corresponding to a ratio of adjuvant to active agrochemical of from about 1:10 to about 500:1. This ratio range will generally be maintained for concentrate forms of formulations e.g. where the adjuvant is included in a dispersible liquid concentrate or dispersible solid granule formulation. However, in using such concentrates, it is possible to add further components, including adjuvants, in tank mixing.

In solid dispersible granules, the proportion of adjuvant will depend on the extent to which relatively inert materials are used to provide the solid structure, but will typically be from 5 to 50% by weight of a dispersible agrochemical granule containing about 1 to 80% by weight of active agrochemical.

In liquid concentrates, particularly emulsifiable concentrates, the proportion of adjuvant will depend on the solubility of the components in the liquid carrier. Typically, the concentration of adjuvant in such a concentrate will be from 1 to 20% by weight in a concentrate containing from 0.2 to 10% by weight of active agrochemical. In some cases the agrochemical is itself a liquid and the concentration of active material in this case can be much higher e.g. up to 90% (in effect the neat material typically including the adjuvant surfactant and usually also emulsifier or dispersant).

The spray formulations will typically have a pH within the range from moderately acid e.g. about 3 to moderately alkaline e.g. about 10, and particular near neutrality, for example 6 to 8.More concentrated formulations will have similar degrees of acidity/alkalinity, but as they may be largely non-aqueous, pH is not necessarily an appropriate measure of this.

The agrochemical composition may include viscosity modifiers, particularly used in emulsifiable concentrates, and/or formulation stabilisers. Known viscosity modifier materials include commercially available water soluble or miscible gums, e.g. xanthan gums, and/or cellulosics, e.g. carboxy-methyl, ethyl or propylcellulose. When used, these are typically used in at from 0.01 to 5% by weight of the total composition (usually the concentrate).

The agrochemical composition may include solvents (other than water) such as monopropylene glycol, oils which can be vegetable or mineral oils such as spray oils (oils included in spray formulations as non-surfactant adjuvants), associated with the adjuvant surfactant. Such solvents may be included as a solvent for the adjuvant surfactant and/or as a humectant e.g. especially propylene glycol. When used such solvents will typically be included in an amount of from 5 to 500%, desirably 10 to 100%, by weight of the adjuvant surfactant. Such combinations can also include salts such as ammonium chloride and/or sodium benzoate and or urea especially as gel inhibition aids.

Particularly when the dispersed phase agrochemical is used in the form of a solution or dispersion in a non-aqueous water immiscible liquid, and particularly in an emulsifyable concentrate, the agrochemical composition will include one or more dispersants and or emulsifiers. These can be conventional surfactant materials as are well known in the art and may be non-ionic, amphoteric, cationic or anionic or combinations of such surfactants. Such materials will typically be included in an amount so as to give a concentration in the spray formulation of from 1 to 30% by weight of the dispersed phase of the spray formulation. As they are included to enhance dispersion, particularly of oily materials e.g. carrier oils, such surfactants may be or include oil soluble surfactants which may be present in a water containing composition, including a spray formulation, between an oil phase and an aqueous phase.

The agrochemical compositions may also include preservatives and/or anti-microbials such as organic acids or their esters or salts such as ascorbic e.g. ascorbyl palmitate, sorbic e.g. potassium sorbate, benzoic e.g. benzoic acid and methyl and propyl 4-hydroxybenzoate, propionic e.g. sodium propionate, phenol e.g. sodium 2-phenylphenate; 1,2-benzisothiazolin-3-one; or formaldehyde as such or as paraformaldehyde; or inorganic materials such as sulphurous acid and its salts, typically in amounts of 0.01 to 1% by weight of the composition and/or antifoam agents e.g. polysilioxane antifoam agents, typically in amounts of 0.005 to 1% by weight of the spray composition.

Other adjuvants, particularly surfactant adjuvants, may be included in the compositions and formulations of and used in this invention. Examples include linear alcohol alkoxylates (as may be present in materials made for use in this invention derived from linear alcohols in the starting materials); alkylpolysaccharides (more property called alkyl oligosaccharides); fatty amine ethoxylates e.g. coconut alkyl amine 2EO; sorbitan and sorbitol ethoxylate derivatives, such as those sold under the trade name Tween by ICI Surfactants; and derivatives of alk(en)yl succinic anhydride, in particular those described in PCT applications WO 94/00508 A and WO 96/16930 A. When used such other adjuvants will typically be used in a ratio of adjuvant surfactant of the formula (I) to the other adjuvant surfactant of 1:10 to 10:1, particularly 5:1 to 1:1 and especially about 3:1.

An increasingly attractive presentation of agrochemical formulations is as solid particles or granules which can be readily dispersed in water to give an application formulation. Plainly it would be desirable to have an adjuvant which could be included in such granular formulations or which can itself be formulated as a dispersible granule, thus enabling the preparation of an agrochemical formulation including an adjuvant by simple mixing of the solid granules (always taking care to avoid undue separation of the solid e.g. arising from density or particle size differences). The surfactant adjuvants of the formula (I) can be formulated in such solid forms. In particular, the adjuvants used in this invention can be formulated to produce water dispersible granules by forming adducts with urea. The invention accordingly includes a water dispersible adduct of a compound of the formula (I) with urea. The adducts with urea are believed to be clathrates (cage compounds) and can be formed by forming a liquid co-melt of the alcohol alkoxylate of the formula (I) with urea and optionally with water and cooling the co-melt to form a solid. To form granular material directly it is desirable to form the co-melt into particles and then to cool it e.g. by spray cooling, particularly by spraying the co-melt into a vessel having a relatively cool gaseous atmosphere and allowing the spray particles to fall under gravity, being cooled by the gaseous atmosphere so that the particles solidify before they reach the base of the vessel. Such particles often take the form of prills.

The solid granules of urea adduct will typically have a ratio of urea to surfactant adjuvant of the formula (I) of from 1:2 to 5:1, particularly 1:1 to 3:1, by weight. As such, even without other components, the granules of adjuvant urea adduct are useful in the formulation of solid/granular agrochemical systems by direct mixing with granular agrochemical active compositions. In use in this way the adjuvant adduct granules will typically be added to water in an amount to provide the desired concentration of adjuvant in the spray formulation, similarly the agrochemical granules will be used in a corresponding amount. The ratio of adjuvant adduct granules to active agrochemical granules will depend on the respective concentrations in the granules as used.

The granules may also include other components of the agrochemical formulation, including the active agrochemical. When the granules contain an active agrochemical the proportion of active agrochemical will typically be from 1 to 30% by weight of the granule. Other possible components of the granules include:

- binders, particularly binders which are readily water soluble to give low viscosity solutions at high binder concentrations, such as polyvinylpyrrolidone; polyvinyl alcohol; carboxymethylcellulose; gum arabic; sugars e.g. sucrose or sorbitol; starch; sucrose and alginates,
- diluents, absorbents or carriers such as carbon black; talc; diatomaceous earth; kaolin; aluminium, calcium or magnesium stearate; sodium tripolyphosphate; sodium tetraborate; sodium sulphate; sodium, aluminium and mixed sodium-aluminium silicates; and sodium benzoate,
- disintegration agents, such as surfactants, materials that swell in water, for example carboxymethyicellulose, collodion, polyvinylpyrrolidone and microcrystalline cellulose swelling agents; salts such as sodium or potassium acetate, sodium carbonate, bicarbonate or sesquicarbonate, ammonium sulphate and dipotassium hydrogen phosphate;
- wetting agents such as alcohol ethoxylate and alcohol ethoxylate/propoxylate wetting agents;
- dispersants such as sulphonated naphthalene formaldehyde condensates and acrylic copolymers such as the comb copolymer having capped polyethylene glycol side chains on a polyacrylic backbone available from ICI Surfactants under the trade name Atlox 4913; and
- antifoam agents, typically at a concentration of from 1 to 10% by weight of the granule;

The spray formulation of adjuvant and active dispersed phase agrochemical in water at application concentration of and used in this invention can be made by a variety of methods. Thus:

i a liquid concentrate containing the active dispersed phase agrochemical dissolved or dispersed in a non-aqueous, water immiscible liquid and optionally including an adjuvant surfactant of the formula (I) can be dispersed into water;

ii a liquid concentrate containing the active dispersed phase agrochemical dissolved or dispersed in a non-aqueous, water miscible liquid, such as N-methylpyrrolidone, and optionally including an adjuvant surfactant of the formula (I) can be dispersed into water (thus precipitating or dispersing the dispersed phase agrochemical in the water);

iii a solid granular concentrate of or containing the active dispersed phase agrochemical and optionally including an adjuvant surfactant of the formula (I) can be dispersed into water, or iv the adjuvant surfactant of the formula (I) can be dispersed into the application formulation, before, at the same time as or after dispersion of the active dispersed phase agrochemical. In this case, the adjuvant surfactant can be the material itself a solution in a solvent (which may be water or a non-aqueous solvent) or a solid granule containing the adjuvant surfactant, in particular a urea adduct of the adjuvant surfactant.

When concentrates (solid or liquid) are used as the source of active agrochemical and/or adjuvant to form the spray formulations the concentrates will typically be diluted with from 10 to 10,000, particularly 30 to 1,000, times the total weight of the agrochemical, adjuvant and any carrier solvent or diluent in the concentrate of water to form the spray formulation for spray application to crops. The invention accordingly includes a spray formulation including at least one dispersed phase agrochemical and as an adjuvant a branched primary alcohol alkoxylate of the formula (I). The spray formulation of the invention may be made by dilution of a concentrate as described above.

The invention further includes a method of treating plants using spray formulations including at least one dispersed phase agrochemical and as an adjuvant a branched primary alcohol alkoxylate of the formula (I). The agrochemical may be one or more phytoactives, for example growth regulators and/or herbicides, and/or pesticides, for example insecticides, fungicides or acaricides. Accordingly the invention further includes method of use including:

i a method of killing or inhibiting vegetation by applying to the vegetation, or the immediate environment of the vegetation e.g. the soil around the vegetation, a spray formulation including at least one dispersed phase agrochemical which is one or more phytoactives, for example growth regulators and/or herbicides, and as an adjuvant a branched primary alcohol alkoxylate of the formula (I); and ii a method of killing or inhibiting pests of plants by applying to the plants or the immediate environment of the plants e.g. the soil around the plants, a spray formulations including at least one dispersed phase agrochemical which is one or more pesticides, for example insecticides, fungicides or acaricides, and as an adjuvant a branched primary alcohol alkoxylate of the formula (1).

Examples of suitable dispersed phase agrochemicals include phytoactives, such as growth regulators and/or herbicides, for example acetochlor, alachlor, nicosulfuron, primisulfuron, prosulfocarb and trifluralin; or pesticides, such as insecticides, for example fenitrothion and propargite, fungicides, for example iprodione and propiconazole, or acaricides.

The following Examples illustrate the invention. All parts and percentages are by weight unless otherwise stated.

Materials

| | |
|---|---|
| Logran | 25% wt active triasulfuron dispersible granules, ex Ciba |
| Allegro | a liquid fungicide formulation containing kresoximm-methyl (125 g.l$^{-1}$) and epoxyconazole (125 g.l$^{-1}$) ex BASF |
| Titus | 25% wt active rimsulfuron dispersible granules ex DuPont |
| Cameo | 75% wt active tribenuron-methyl dispersible granules, ex DuPont |

Conventional Adjuvants

| | |
|---|---|
| Trend 90 | isodecyl alcohol ethoxylate ex DuPont |
| Synperonic 13/9 | tridecanol 9EO alcohol ethoxylate ex ICI Surfactants |
| Atplus 435 | Alkylpolysacharide adjuvant ex ICI Surfactants |
| NP8 | nonyl phenol 8-ethoxylate |

Branched primary alcohols

| | |
|---|---|
| AL1 | 2-butyloctanol made by the guerbet process |
| AL2 | mixture of primary alcohols mainly having 12 to 15 carbon atoms |

-continued

| | |
|---|---|
| | and containing about 50% monobranched primary alcohol and about 50% linear primary alcohol made by the oxo process from internal olefin precursors |

Branched primary alcohol alkoxylate adjuvant surfactants:

| | |
|---|---|
| AS1 | 9-ethoxylate/3-propoxylate block copolymer of AL1 |
| AS2 | 7-ethoxylate of AL1 |
| AS3 | 8-ethoxylate of AL2 |
| AS4 | mixture of AS2 (70%) and monopropylene glycol (30%) by weight |
| AS5 | 9-ethoxylate of AL1 |
| AS6 | dispersible granules of AS5 and urea (see Example 3a) |

General Methods

Field tests were carried out on test plots using a completely randomised block design with 4 replicates. The spray volume used was 300 l.ha$^{-1}$. Control runs using adjuvant at 0.1% in water (no active agrochemical) were run in each experimental sequence and showed that on their own they were not phytotoxic and have no agrochemical activity.

EXAMPLE 1

Triasulfuron is a selective sutfonylurea herbicide which is known to have limited activity against weeds such as cleavers (*Galium aparine*) and ivy-leaved speedwell (*Veronica hederifolia*), in particular giving low necrosis (killing) rates. In such a situation, it is an important benefit if the herbicide can limit the growth of the weeds (inhibition) e.g. by use of an adjuvant. In this Example, the effect of adjuvants on the activity of triasulfuron against *G aparine* and *V hederifolia* growing naturally as weeds in winter wheat was examined. Treatment formulations were made up using a dispersion of triasulfuron at a concentration of 3.3% by weight (0.83% by weight of active). Various adjuvants were added to the dilute dispersion at a concentration of 0.1% by weight and control runs including no adjuvant. The plots were sprayed at a dose rate of active triasulfuron of 25 g.ha$^{-1}$.

Chlortoluron (1500 g.ha$^{-1}$) had been used as a preemergence herbicide. *G aparine* and *V hederifolia* were used in evaluating herbicidal activity because of their regular distribution. The herbicidal effect on the weeds and any crop damage were evaluated visually 1, 2, 5 and 7 weeks after treatment and the extent of inhibition, chlorosis and necrosis expressed as percentages of plants affected. The results of the runs using no adjuvant and those for combined adjuvants and herbicide are set out in Table 1 below.

TABLE 1

| | *Veronica hederifolia* (5 weeks) | | | *Galium aparine* (5 weeks) | | |
|---|---|---|---|---|---|---|
| Adjuvant | Inhibition | Chlorosis | Necrosis | Inhibition | Chlorosis | Necrosis |
| none | 40 | 10 | 10 | 50 | 30 | 10 |
| Atplus 435 | 60 | 50 | 20 | — | — | — |
| NP8 | 60 | 40 | 30 | 40 | 30 | 10 |
| AS2 | 70 | 50 | 20 | 60 | 50 | 20 |

These data indicate that the inclusion of AS2 as an adjuvant gave good growth inhibition of *G aparine* and *V hederifolia*. It was superior to the other adjuvants and markedly superior to the control runs using no adjuvants.

EXAMPLE 2

This Example shows the effectiveness of the adjuvants in obtaining enhanced effectiveness of agrochemicals at lower than usual application rates. Tests were run to examine the activity of fungicides against powdery mildew (*Erysiphe graminis*) and leaf spot (*Septoria tritici*) in wheat. The tests were earned out using a completely randomised block design with 4 replicates on a clay soil. An advance crop of maize was grown as a sowing density of 400 kemels.m$^2$, a nitrogen fertiliser application of 68 kg.ha$^{-1}$, a herbicide application of Defi+AZ500+Prodix at (5l+150 ml+1.5 l).ha$^{-1}$ (respectively) and using Meteor at 2 l.ha$^{-1}$ as growth regulator. The subsequent wheat crop was subject to adventitious infection of *S tritici* and *E graminis* and were spray treated with the fungicidal sprays set out below.

The spray formulation was made up to contain 0.042% active fungicides (equivalent to an application rate of Allegro of 1 l.ha$^{-1}$. When used, adjuvants were incorporated in the tank mix at 0.1% of the spray. Tests were run using:

the fungicide (no adjuvant) at its normal application rate (250 g.ha$^{-1}$ total actives)

the fungicide (no adjuvant) at 75% of its normal application rate the fungicide at 75% of its normal application rate plus 0.1% (on spray) of adjuvant untreated control The effect of the treatments was assessed visually. For *S tritici* the leaves were observed separately and the percentage of the area of infected 2nd and 3rd leaves was determined. For *E graminis* the percentage infection was assessed. When the crop was sprayed, only a very slight infection was apparent. The results are set out in Table 2 below.

TABLE 2

| Treatment | S tritici 2nd leaf | S tritici 3rd leaf | E graminis |
|---|---|---|---|
| NAR | 5.8 | 13.3 | 50 |
| 75% NAR | 5 | 13.3 | 27 |
| 75% NAR + 0.1% AS1 | 2.5 | 5.8 | 10 |
| 75% NAR + 0.1% AS2 | 4.2 | 8.3 | 10 |
| 75% NAR + 0.1% AS4 | 6.7 | 11.7 | 10 |
| Untreated control | 18.3 | 28.3 | 50 |

In general, the level of infection was low and the relatively dry growing conditions meant that even the fungicide alone at 75% NAR gave good results. Even so, the inclusion of the adjuvants gave better disease control for both fungus infections. The combinations using the adjuvants AS1 and AS2 gave particularly good results in suppressing S tritici as well as E graminis.

EXAMPLE 3a

This Example illustrates the production of a urea adduct of a surfactant adjuvant of the formula (I). Adjuvant AS5 (120 g) and urea (180 g) were heated together at 140° C. to form a homogeneous co-melt which was sprayed into an air atmosphere at ambient temperature to cool and solidify it. The product adduct (300 g) was collected as solid granules having an average particle size of 0.2 to 2 mm containing 60% by weight urea and 40% by weight AS5.The granules were readily dispersible into water on mixing and simple stirring to give a solution of surfactant adjuvant in water at a concentration of 0.1% by weight.

EXAMPLE 3b

This Example illustrates the formulation of the adjuvants as solids which can be mixed with the active in solid form or added to a tank mix (including the urea adduct made in Example 3a). The agricultural target was the control of Echinochloa crus-galli in growing maize using Titus dry granules. The spray was made up containing 0.0033% active rimsulfuron—equivalent to an application rate of 40 g.ha$^{-1}$. Adjuvant AS1 was added as adjuvant to the tank mix at 0.1% on the spray and adjuvant AS6 was added as a dry granule with the Titus granules to the water in the spray tank. The test plots were assessed visually 2, 3 and 4 weeks after spraying on a 0 to 100% linear scale (0=no effect; 100=complete weed control)

Because the sulfonylurea herbicide is a post-emergence selective herbicide especially used to control specific weeds which escape from traditional herbicides, a pre-emergence soil-applied herbicide was used to obtain better general control. The results are set out in Table 3 below

TABLE 3

| Adjuvant | % control of E crus-galli 2 weeks | 3 weeks | 4 weeks |
|---|---|---|---|
| Untreated | 0 | 0 | 0 |
| None | 20 | 38 | 55 |
| Synperonic 13/9 | 29 | 59 | 74 |
| Trend 90 | 28 | 55 | 71 |
| AS1 | 25 | 49 | 70 |
| AS6 | 30 | 65 | 74 |

With rimsulfuron as active, adjuvant AS1 gave the best performance against E crus-galli. The solid adjuvant, AS6 gave excellent control, especially as the product contains only 40% active adjuvant.

EXAMPLE 4

This Example shows the effectiveness of the adjuvants in the use of Cameo (tribenuron-methyl) as a herbicide in the control of Veronica hederffolia in winter wheat under field conditions. The spray solution contained 0.015% by weight tribenuronethyl and 0.1% adjuvant added to the tank mix. The effectiveness of the herbicides was assessed visually by the % growth reduction of the weeds as compared with untreated weeds. The results are given in Table 4 below.

The uptake of the active herbicide into the leaves of the V hededfolia was assessed from samples taken immediately, 1 and 4 hours after spraying. 50 g of plants were taken at random over the replicate plots and cut off just above the soil surface. The leaves were rinsed with 50 ml distilled water and the washings used to assay for the herbicide present on the leaf surface and the washed leaves were then rinsed in 50 ml chloroform to dissolve the waxy leaf cuticle. Assay of the active herbicide was carried out by HPLC. The amount of active herbicide detected in the wax cuticle [expressed as $\mu g(adjuvant).g(leaf)^{-1}$] is included in Table 4.

TABLE 4

| Adjuvant | Inhibition (%) | Time (h) | amount ($\mu$g.g$^{-1}$ leaf) |
|---|---|---|---|
| none | 18 | 0 | n.d.* |
|  |  | 1 | 0.001 |
|  |  | 4 | 0.005 |
| NP8 | 33 | — | — |
| AS2 | 41 | 0 | n.d.* |
|  |  | 1 | 0.080 |
|  |  | 4 | 0.120 | n.d.* : not detectable (<0.001)

These data show that the active ingredient is absorbed the wax layer of V hederifolia after 4 hours, but with the commercial formulation (Cameo) this accumulation was very limited. The inclusion of the adjuvants enhanced the accumulation of the active in the wax.

What is claimed is:

1. An aqueous agrochemical composition consist essenitially of a dispersed phase agrochemical and as an adjuvant a branched primary alcohol alkoxylate of the formula (I):

[CH$_3$.(CH$_2$)$_n$][CH$_3$.(CH$_2$)$_m$].CH.[(CH$_2$)$_p$.O.(AO)$_q$.H]   (I)

where n and m are each independently from 1 to 13; and p is 1 or 2; such that n+m+p is from 8 to 18;

AO is an alkylene oxide residue having from 2 to 4 carbon atoms; and q is from 2 to 30.

2. An agrochemical composition as claimed in claim 1 wherein n and m are each independently at least 2 and not more than 12; p is 1 and the total number of carbon atoms in the branched alkyl residue is desirably from 10 to 14.

3. An agrochemical composition as claimed in claim 1 wherein the alkylene oxide groups are all ethylene oxide residues or mixtures of ethylene oxide and propylene oxide residues; and q is 5 to 20.

4. An agrochemical composition as claimed in claim 1 wherein the agrochemical is present in solid particles or dissolved or dispersed in an oil.

5. An agrochemical composition as claimed in claim 1 wherein the weight ratio of adjuvant surfactant of the formula (I) to active agrochemical of from 1:10 to 500:1.

6. An agrochemical composition as claimed in claim 5 wherein the agrochemical is present in dispersible solid granules containing from 1 to 80% by weight of active agrochemical and the adjuvant surfactant of the formula (I) is present as from 5 to 50% by weight of the granules.

7. An agrochemical composition as claimed in claim 5 wherein the agrochemical is present in a liquid concentrate containing from 0.2 to 10% by weight of active agrochemical and from from 1to 20% by weight of the concentrate of an adjuvant surfactant of the formula (I).

8. An agrochemical composition as claimed in claim 5 in the form of a sprayable aqueous dispersion containing the agrochemical at a concentration of from 0.001 to about 1% by weight of the spray formulation and adjuvant surfactant of the formula (I) in a concentration of from 0.01 to 2% by weight of the spray formulation.

9. The agrochemical composition according to claim 1, wherein the dispersed phase agrochemical is acetochlor, alachlor, nicosulfuron, primisulfuron, prosulfocarb or trifluralin.

10. The agrochemical composition according to claim 1, wherein the dispersed phase agrochemical is a pesticide.

11. A water dispersible agrochemical composition which includes a dispersed phase agrochemical and including a branched primary alcohol alkoxylate of the formula (I):

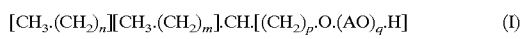

$$[CH_3.(CH_2)_n][CH_3.(CH_2)_m].CH.[(CH_2)_p.O.(AO)_q.H] \quad (I)$$

where n and m are each independently from 1 to 13; and p is 1 or 2; such that n+m+p is from 8 to 18;

AO is an alkylene oxide residue having from 2 to 4 carbon atoms; and q is from 2to 30, present as solid granules of a urea adduct, as an adjuvant.

12. A composition as claimed in claim 11 wherein the weight ratio of urea to surfactant adjuvant of the formula (I) of from 1:2 to 5:1.

13. A composition as claimed in claim 9 which at least part of the active agrochemical is included in the urea adduct.

14. An agrochemical composition as claimed in claim 1 wherein the dispersed phase agrochemical is one or more of acetochtor, alachlor, nicosulfuron, primisulfuron, prosulfocarb, trifluralin, fenitrothion, propargite, iprodione and propiconazole.

15. A sprayable agrochemical composition which comprises at least one dispersed phase agrochemical and as an adjuvant a branched primary alcohol alkoxylate of the formula (I) as defined in claim 1.

16. A method of treating plants which comprises applying to the plants, or the immediate environment of the plants a sprayable formulation as claimed in claim 15.

17. A method as claimed in claim 16 for killing or inhibiting vegetation by applying to the vegetation, or the immediate environment of the vegetation a spray formulation as claimed in claim 13 which includes at least one dispersed phase agrochemical which is one or more growth regulator(s) and/or herbicide(s).

18. A method as claimed in claim 16 for killing or inhibiting pests of plants by applying to the plants or the immediate environment of the plants a spray formulation as claimed in claim 13 which includes at least one dispersed phase agrochemical which is one or more insecticide(s), fungicide(s) or acaricide(s).

19. A method as claimed in claims 14 in which the dispersed phase agrochemical is one or more of acetochlor, alachlor, nicosulfuron, primisulfuron, prosulfocarb, trifluralin, fenitrothion, propargite, iprodione and propiconazole.

* * * * *